(12) United States Patent
Lee et al.

(10) Patent No.: US 9,247,893 B2
(45) Date of Patent: Feb. 2, 2016

(54) SENSOR FOR MICROWAVE IMAGE

(71) Applicant: Electronics and Telecommunications Research Institute, Daejeon (KR)

(72) Inventors: Kwang Jae Lee, Daejeon (KR); Soon Ik Jeon, Daejeon (KR); Jong Moon Lee, Daejeon (KR); Jang Yeol Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 135 days.

(21) Appl. No.: 14/090,031

(22) Filed: Nov. 26, 2013

(65) Prior Publication Data

US 2014/0309528 A1 Oct. 16, 2014

(30) Foreign Application Priority Data

Apr. 16, 2013 (KR) .................. 10-2013-0041652

(51) Int. Cl.
*A61B 5/05* (2006.01)
*A61B 5/00* (2006.01)

(52) U.S. Cl.
CPC ............. *A61B 5/0507* (2013.01); *A61B 5/4312* (2013.01); *A61B 2562/0228* (2013.01); *A61B 2562/043* (2013.01); *A61B 2562/143* (2013.01); *A61B 2562/168* (2013.01)

(58) Field of Classification Search
CPC ................. A61B 2562/0228; A61B 2562/043; A61B 2562/143; A61B 2562/168; A61B 5/0507; A61B 5/4312
See application file for complete search history.

(56) References Cited

U.S. PATENT DOCUMENTS

| 2004/0077943 | A1 | 4/2004 | Meaney et al. | |
|---|---|---|---|---|
| 2009/0027288 | A1* | 1/2009 | Lee et al. | ............ 343/766 |
| 2013/0141794 | A1* | 6/2013 | Najiminaini et al. | ......... 359/634 |

FOREIGN PATENT DOCUMENTS

| JP | 2009219837 A | 10/2009 |
|---|---|---|
| KR | 1020100068542 A | 6/2010 |

* cited by examiner

*Primary Examiner* — Michael Rozanski
(74) *Attorney, Agent, or Firm* — William Park & Associates Ltd

(57) ABSTRACT

A sensor includes a tank filled with a matching medium, a metal body configured to surround an image object received in the tank, and a plurality of apertures disposed at constant intervals inside the metal body, wherein when any one of the plurality of apertures radiates microwaves to the image object, remaining apertures receive scattering microwaves from the image object.

18 Claims, 13 Drawing Sheets

SENSOR FOR MICROWAVE IMAGE

RELATED APPLICATION(S)

This application claims the benefit of Korean Patent Application No. 10-2013-0041652, filed on Apr. 16, 2013, which is hereby incorporated by references as if fully set forth herein.

FIELD OF THE INVENTION

The present invention relates to a sensor for a microwave image, and more particularly, to a sensor for a microwave image, which is suitable for radiating microwaves to the object whose image will be obtained in order to diagnose an image of human tissue and sensing (receiving) scattering microwaves from the object whose image will be obtained.

BACKGROUND OF THE INVENTION

As well known, a human tissue image diagnostic apparatus (e.g., a breast cancer diagnostic apparatus) using microwaves is an apparatus for obtaining an image by radiating microwaves to the object whose image will be obtained. The apparatus is a medical apparatus in which when microwaves output from an output device pass through the object whose image will be obtained (e.g., a breast in the case of a breast cancer image diagnostic apparatus), an input device obtains information on the size and phase of a scattering signal (i.e., scattering microwaves), restores an image through an inverse scattering analysis based on the obtained information, and diagnoses whether or not cancer is present and the size and location of cancer from the restored image.

FIG. 1 shows the structure of a conventional breast cancer image diagnostic apparatus using a plurality of transmission and reception sensors (Meaney et al., Systems and Methods for 3-D Data Acquisition for Microwave Imaging, U.S. patent application Ser. No. 10/407,886, Apr. 4, 2003).

Referring to FIG. 1, in a conventional breast cancer image diagnostic apparatus, a plurality of transmission and reception sensors 100 #1-#N that are circularly arranged is fixed and disposed, and the breast 101 of an examinee is inserted between the sensors.

Thereafter, one (e.g., #1) of the plurality of sensors sends microwaves 102, receives microwave signals 103 scattered from the remaining sensors, and obtains information on the sizes and phases of the received microwave signals. Thereafter, the sensor #2 at another location sends microwaves, and the remaining sensors receive scattered microwave signals. This process is repeatedly performed up to the last sensor #N.

The conventional breast cancer image diagnostic apparatus restores a breast tomographic image of the examinee through a microwave inverse scattering analysis based on information on the size and phase of microwaves obtained from the sensors. In particular, when tumor tissue 104 having electrical characteristics (e.g., a dielectric constant and conductivity) different from those of breast tissue is present in the breast of the examinee, information on a received microwave signal is different from that when tumor tissue is not present, and whether or not a tumor is present within the breast is diagnosed based on the information.

As described above, in the prior art, an image is restored by fixing and disposing a plurality of transmission and reception sensors at constant intervals around the breast. Furthermore, in order to restore a three-dimensional (3-D) image, a task for vertically moving the sensors also needs to be performed.

SUMMARY OF THE INVENTION

In view of the above, the present invention provides a new scheme which can obtain high-precision image results from microwaves that are intensively radiated from a sensor for a microwave image to the object whose image will be obtained (also called an image object) of the human body, obtain an image of human tissue for an image diagnosis having adaptability to the size and shape of the image object, and effectively obtain a 3-D image of human tissue through a sensor having a 3-D structure.

In accordance with an aspect of the exemplary embodiment of the present invention, there is provided a sensor for a microwave image, which includes a tank filled with a matching medium, a metal body configured to surround an image object received in the tank, and a plurality of apertures disposed at constant intervals inside the metal body, wherein when any one of the plurality of apertures radiates microwaves to the image object, remaining apertures receive scattering microwaves from the image object.

In the exemplary embodiment, the matching medium may has a dielectric constant identical with a dielectric constant of the image object.

In the exemplary embodiment, the matching medium may be a loss matching medium of a liquid phase.

In the exemplary embodiment, the matching medium may be a non-loss matching medium of gas or a dielectric solid.

In the exemplary embodiment, the metal body may senses an image of the image object through a rotational movement and a vertical movement.

In the exemplary embodiment, the metal body may has a ring-shaped structure or a polygonal structure.

In the exemplary embodiment, the inside of the metal body may be configured to have edge angles formed by mountains and valleys.

In the exemplary embodiment, the inside of the metal body may has a wrinkle structure.

In the exemplary embodiment, if the metal body has the polygonal structure, a receipt width of the image object may be changed by partial folding based on at least any one of the plurality of apertures.

In the exemplary embodiment, the image object may be any one of human tissues for an image diagnosis.

In accordance with another of the exemplary embodiment of the present invention, there is provided a sensor for a microwave image, which includes a tank filled with a matching medium, and a body structure configured to comprise metal bodies, the metal bodies formed in plural layers and configured to have a plurality of apertures disposed at constant intervals inside the metal body, to surround an image object received in the tank, and to have remaining apertures received scattering microwaves from the image object when any one of the plurality of apertures radiates microwaves to the image object.

In the exemplary embodiment, each of the metal bodies forming the body structure may be configured to rotationally move in a direction different from a direction of a neighboring metal body.

In the exemplary embodiment, the body structure may senses an image of the image object through a rotational movement and a vertical movement.

In the exemplary embodiment, the body structure may has a ring-shaped structure or a polygonal structure.

In the exemplary embodiment, the inside of each of the metal bodies forming the body structure may be configured to have edge angles formed by mountains and valleys.

In the exemplary embodiment, the inside of each of the metal bodies forming the body structure may be configured to have a wrinkle structure.

BRIEF DESCRIPTION OF THE DRAWINGS

The objects and features of the present invention will become apparent from the following description of embodiments given in conjunction with the accompanying drawings, in which.

DETAILED DESCRIPTION OF THE EMBODIMENTS

First, the merits and characteristics of the present invention and the methods for achieving the merits and characteristics thereof will become more apparent from the following embodiments taken in conjunction with the accompanying drawings. However, the present invention is not limited to the disclosed embodiments, but may be implemented in various ways. The embodiments are provided to complete the disclosure of the present invention and to enable a person having ordinary skill in the art to understand the scope of the present invention. The present invention is defined by the claims.

In describing the embodiments of the present invention, a detailed description of known functions or constructions related to the present invention will be omitted if it is deemed that such description would make the gist of the present invention unnecessarily vague. Furthermore, terms to be described later are defined by taking the functions of embodiments of the present invention into consideration, and may be different according to the operator's intention or usage. Accordingly, the terms should be defined based on the overall contents of the specification. Hereinafter, embodiments of the present invention will be described in detail with reference to the accompanying drawings which form a part hereof.

Embodiment 1

Figure 1:
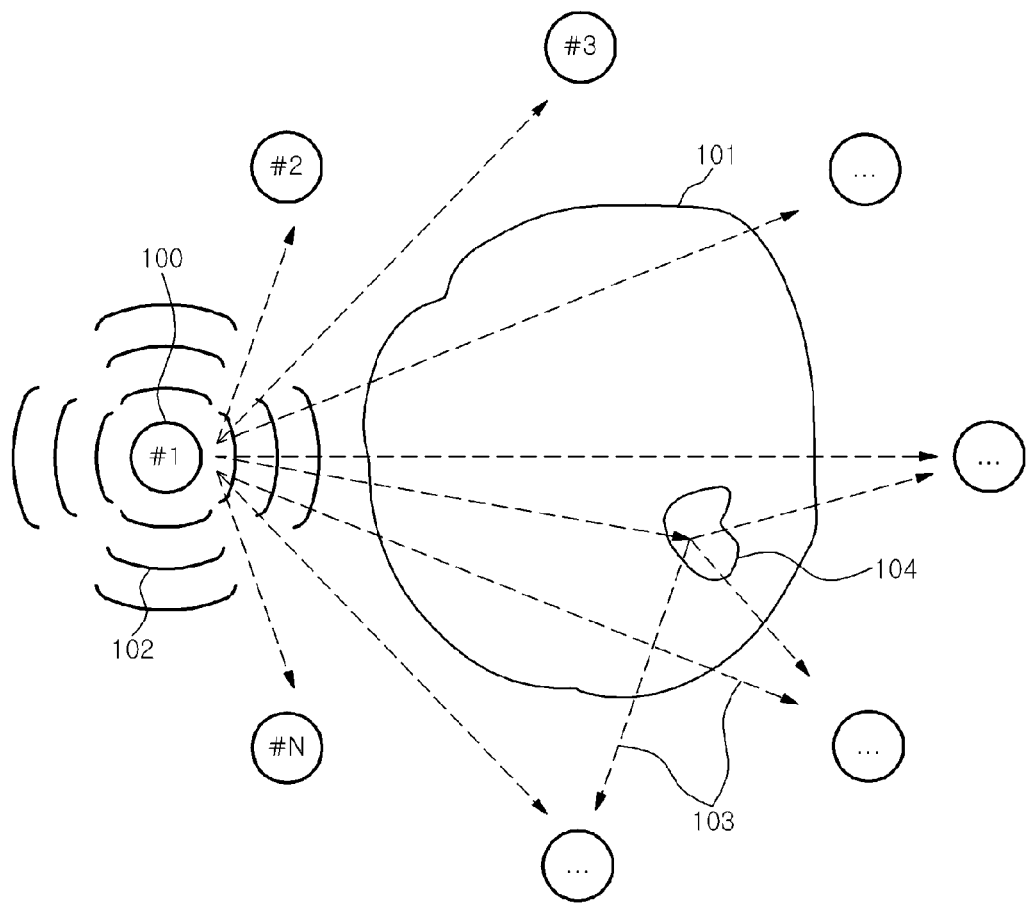
FIG. 1 shows the structure of a conventional breast cancer image diagnostic apparatus using a plurality of transmission and reception sensors.
Figure 2A:
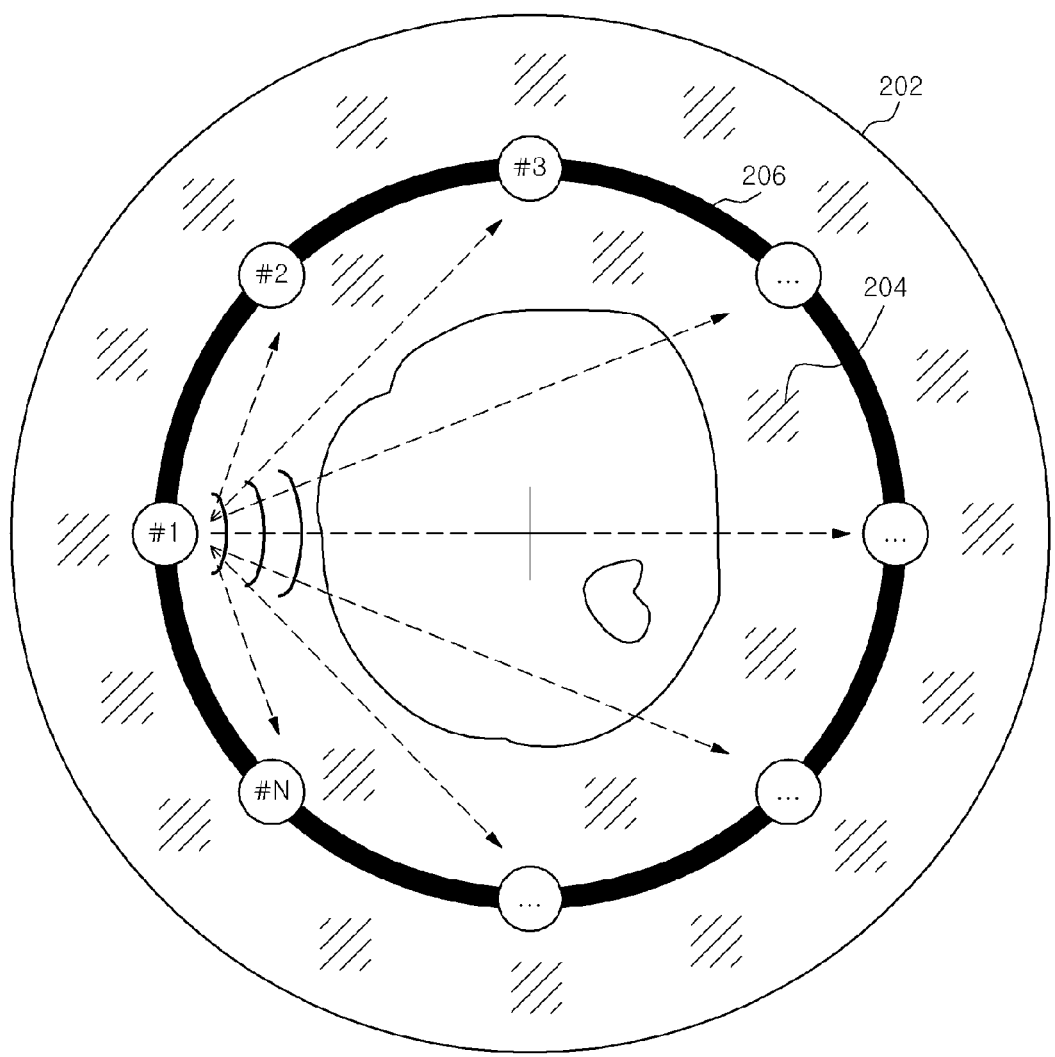
FIGS. 2a to 2d are diagrams illustrating the structure of a sensor for a microwave image and a method of sensing a microwave image in accordance with embodiments of the present invention.
Figure 2B:
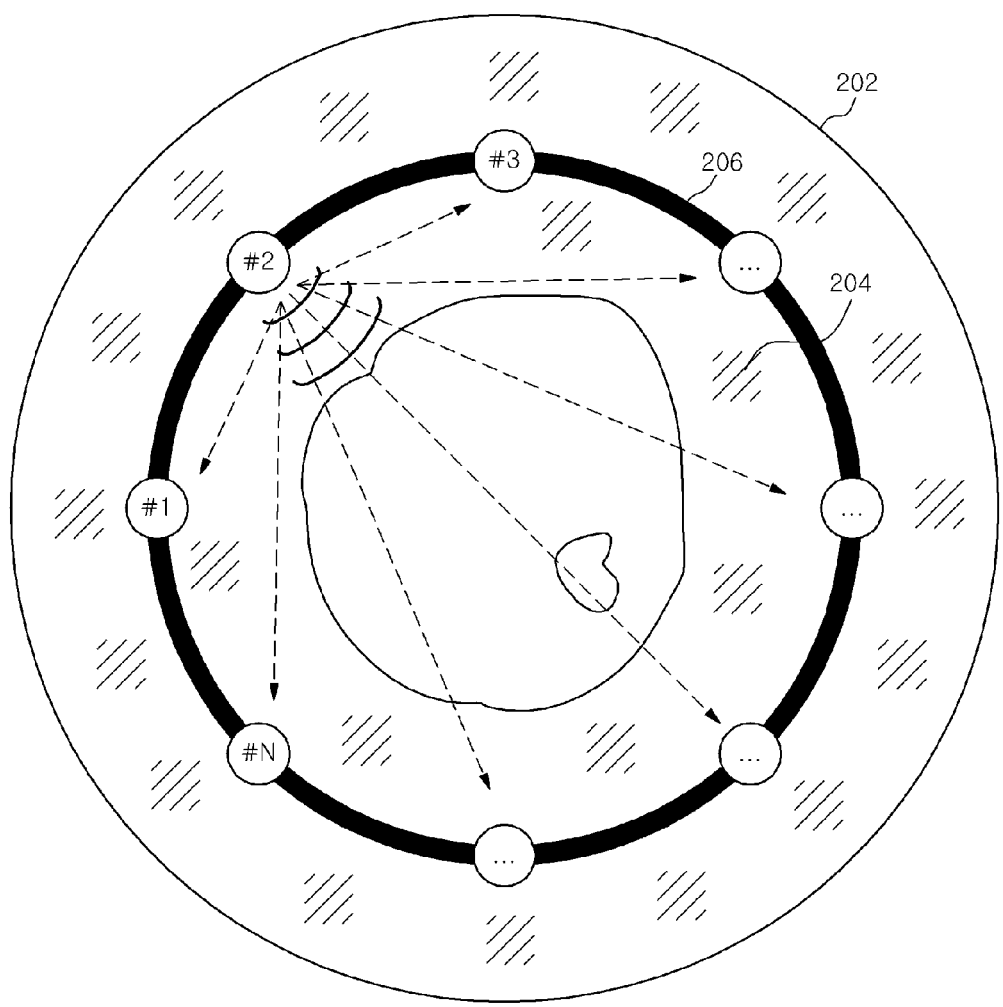
Figure 2C:
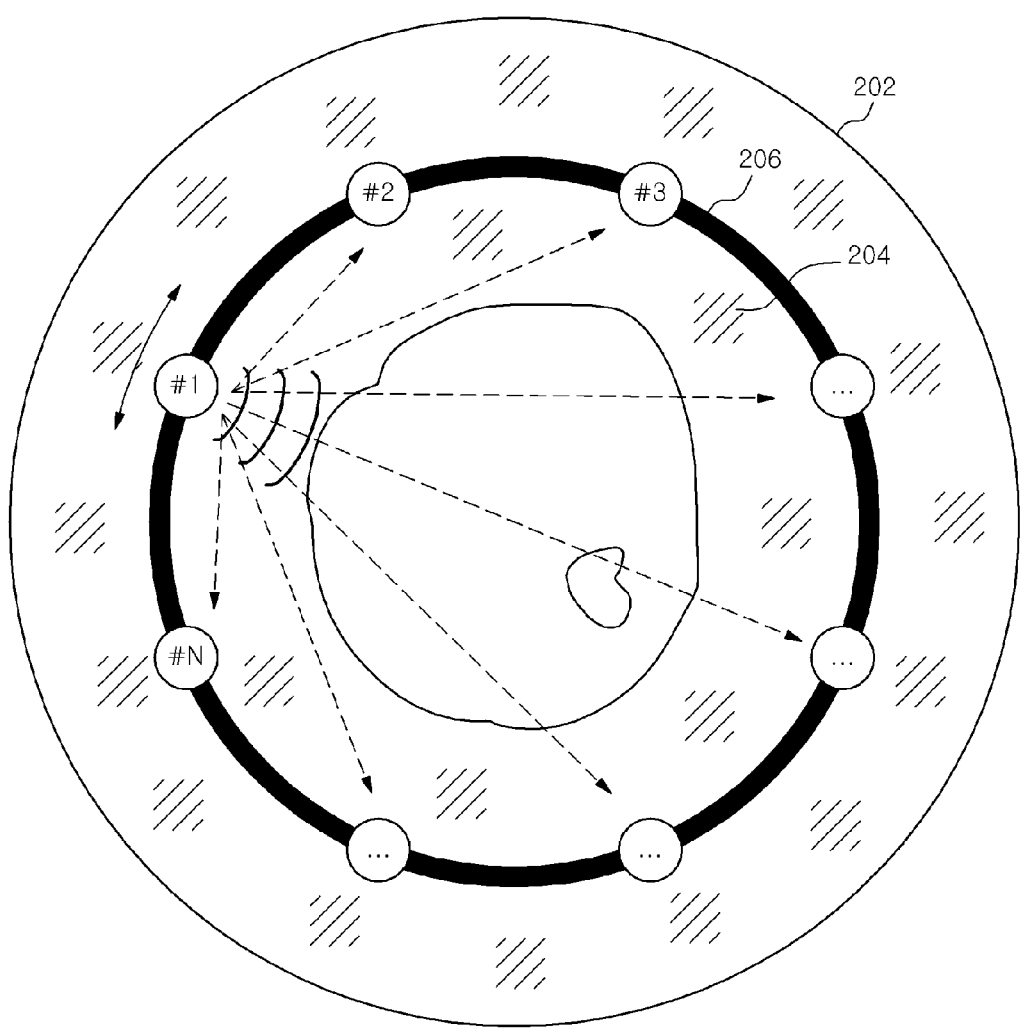
Figure 2D:
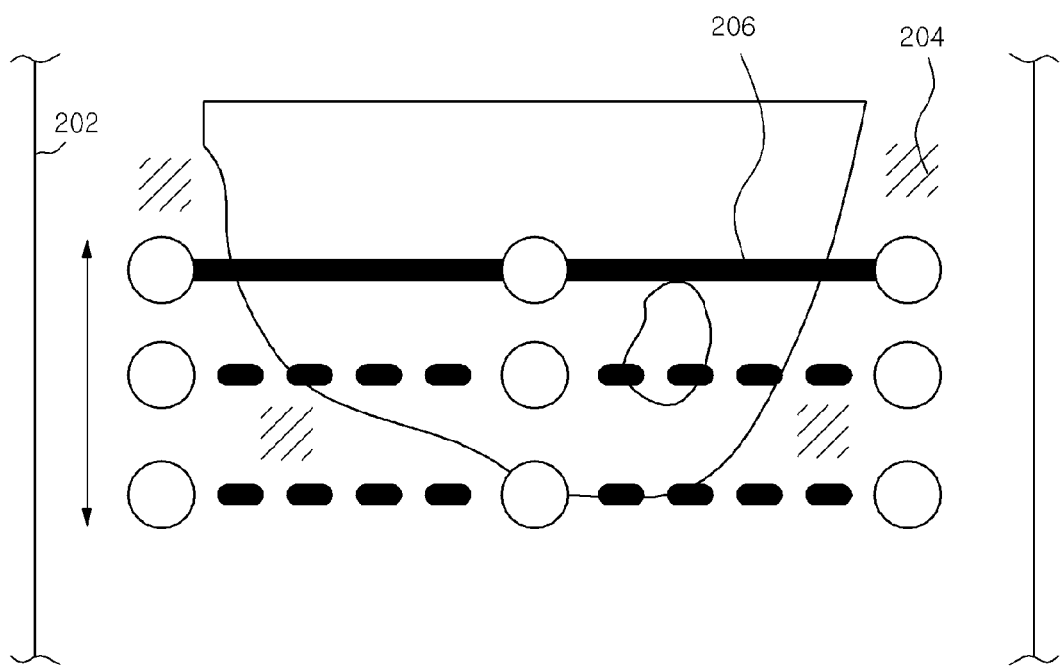
Figure 3:
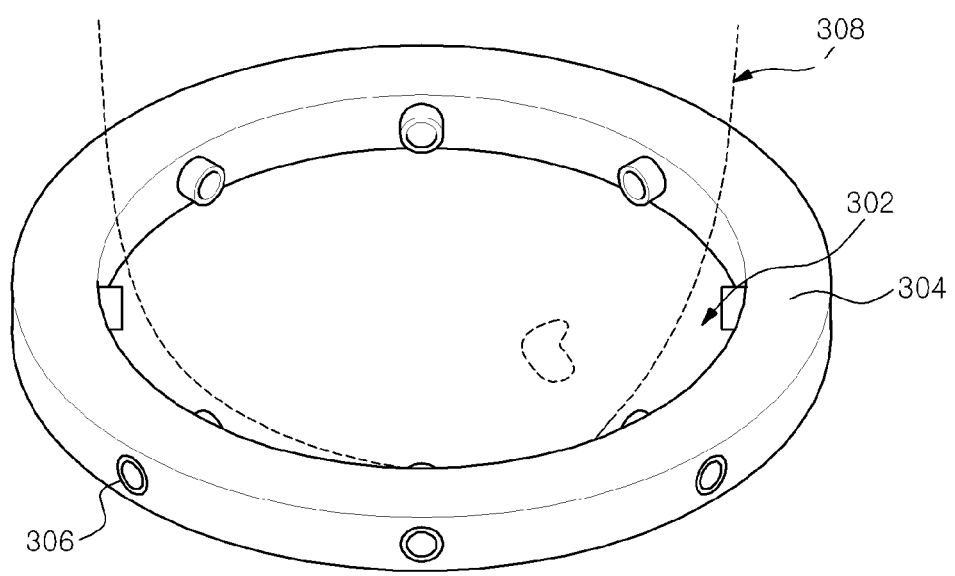
FIG. 3 shows the structure of a sensor for a microwave image in accordance with an embodiment of the present invention.

FIGS. 2a to 2d are diagrams illustrating the structure of a sensor for a microwave image and a method of sensing a microwave image in accordance with embodiments of the present invention, and FIG. 3 shows the structure of a sensor for a microwave image in accordance with an embodiment of the present invention.

Referring to FIG. 2a, the sensor for a microwave image in accordance with the present embodiment may include a tank 202 configured to have a matching medium 204 filled therein, a metal body 206 configured to surround an image object received in the tank 202, and a plurality of apertures #1 to #N disposed (i.e., fixed and disposed) at constant intervals inside the metal body 206. The matching medium may have the same dielectric constant as the image object (e.g., human tissue, such as the breast whose image needs to be diagnosed). The matching medium may be a loss matching medium of a liquid phase (liquid) or a non-loss matching medium of gas or a dielectric solid.

That is, the metal body 206 forms an integral structure for connecting the plurality of apertures #1 to #N formed at constant intervals inside the metal body. For example, as shown in FIG. 3, each of the apertures #1 to #N may have a cylindrical and projected (or protruded) aperture shape having a relatively narrower beam width and higher gain characteristic as compared with a conventional sensor. In FIG. 3, reference numeral 302 denotes a matching medium, 304 denotes a metal body, 306 denotes an aperture, and 308 denotes the breast that can be defined as an image object.

Furthermore, the image object is received in the tank 202 formed to surround the metal body 206. Each of the apertures #1 to #N formed at constant intervals inside the metal body 206 provides a function of inputting and outputting microwaves (i.e., radiating the microwaves and receiving scattering microwaves). When any one of the plurality of apertures radiates (transmits) microwaves to the image object, the remaining apertures can receive scattering microwaves (i.e., scattering information) (i.e., sense an image of the image object) from the image object.

For example, as shown in FIG. 2a, when the aperture #1 radiates (transmits) microwaves to the image object, the remaining apertures #2 to #N receive scattering microwaves that are scattered through the image object. For example, as shown in FIG. 2b, when the aperture #2 radiates (transmits) microwaves to the image object, the remaining apertures #1 and #3 to #N receive scattering microwaves that are scattered through the image object (i.e., sense an image of the image object).

To this end, for example, as shown in FIG. 2c, the metal body 206 can be configured to be rotationally moved (i.e., a clockwise or counterclockwise rotational movement indicated by an arrow), or the aperture for radiating microwaves can be configured to switch clockwise or counterclockwise (i.e., sequentially radiate microwaves in order of #1, #2, #3, #4, m #5 . . . ).

Furthermore, the metal body 206 is configured to perform a vertical movement along with a rotational movement. In this case, an image of the image object can be sensed (or obtained) in a 3-D structure by scanning the microwaves through the vertical movement (i.e., scanning the microwaves for the image object), for example, as shown in FIG. 2d.

A ring-shaped structure can be applied to the metal body 304 in which the plurality of apertures is formed therein at constant intervals, for example, as shown in FIG. 3. Each of the apertures 306 formed (fixed and disposed) at constant intervals inside the metal body 304 may have a cylindrical and projected (protruded) aperture structure. In accordance with such a structure, microwaves can be intensively radiated to the image object 308 received in the tank 302 (i.e., radiate microwaves having a relatively narrow beam width).

Figure 4A:
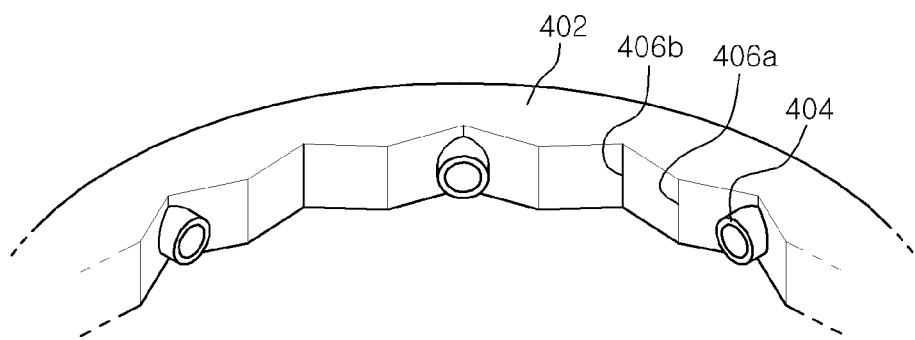
FIGS. 4a to 4c show partial cutout structures of a modified example of a sensor for a microwave image in accordance with an embodiment of the present invention.
Figure 4B:
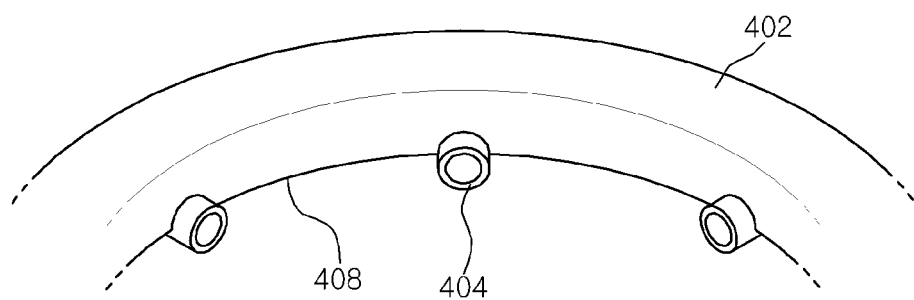
Figure 4C:
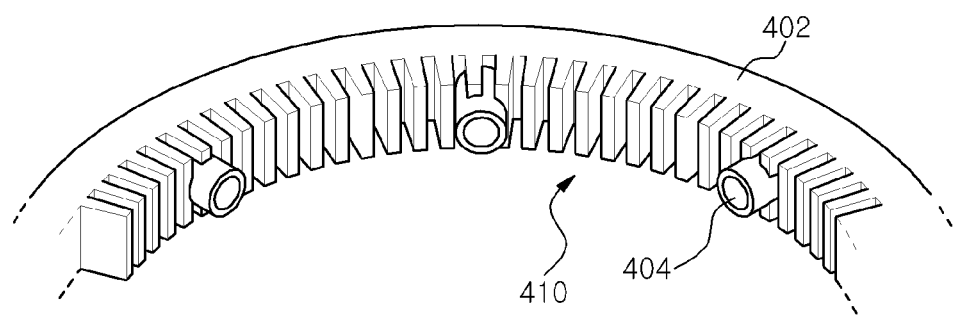

In an embodiment, for example, as shown in FIGS. 4a to 4c, a structure for preventing the scattering, diffraction, and reflection phenomena of microwaves toward other parts other than an image object may be applied to the inside of the metal body which is applied to the sensor for a microwave image in accordance with the present embodiment. The scattering, diffraction, and reflection phenomena of microwaves from other parts other than the image object act as errors and noise components. Such a structure prevents an error in reading the final image.

FIGS. 4a to 4c show partial cutout structures of a modified example of the sensor for a microwave image in accordance with an embodiment of the present invention.

Referring to FIG. 4a, the inside of a metal body 402 may be configured to have an edge angle formed by a mountain 406a and a valley 406b between adjacent apertures 404. As shown in FIG. 4b, an approximately central part of the inside of a metal body 402 that connects neighboring apertures 404 may be configured to form a mountain 408. For example, as shown in FIG. 4c, the front of the inside of the metal body 402 may be configured to have a wrinkle structure (or wrinkle shape) 410.

Figure 5:
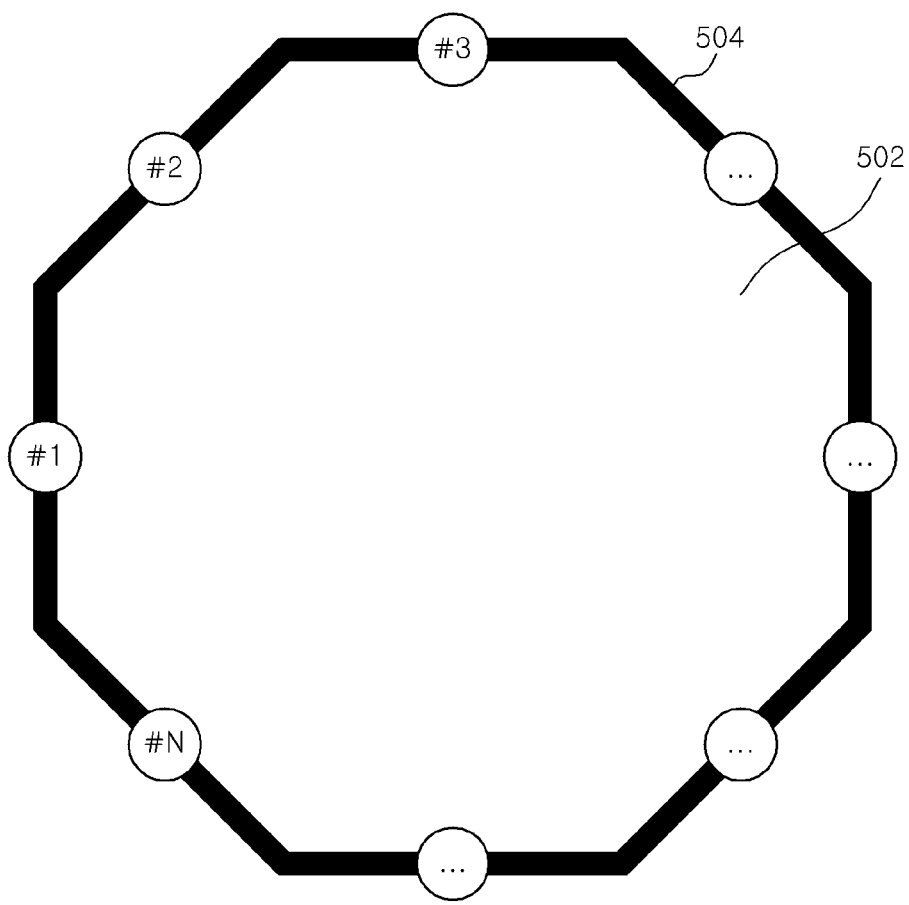
FIG. 5 shows the structure of a sensor for a microwave image in accordance with another embodiment of the present invention.
Figure 6:
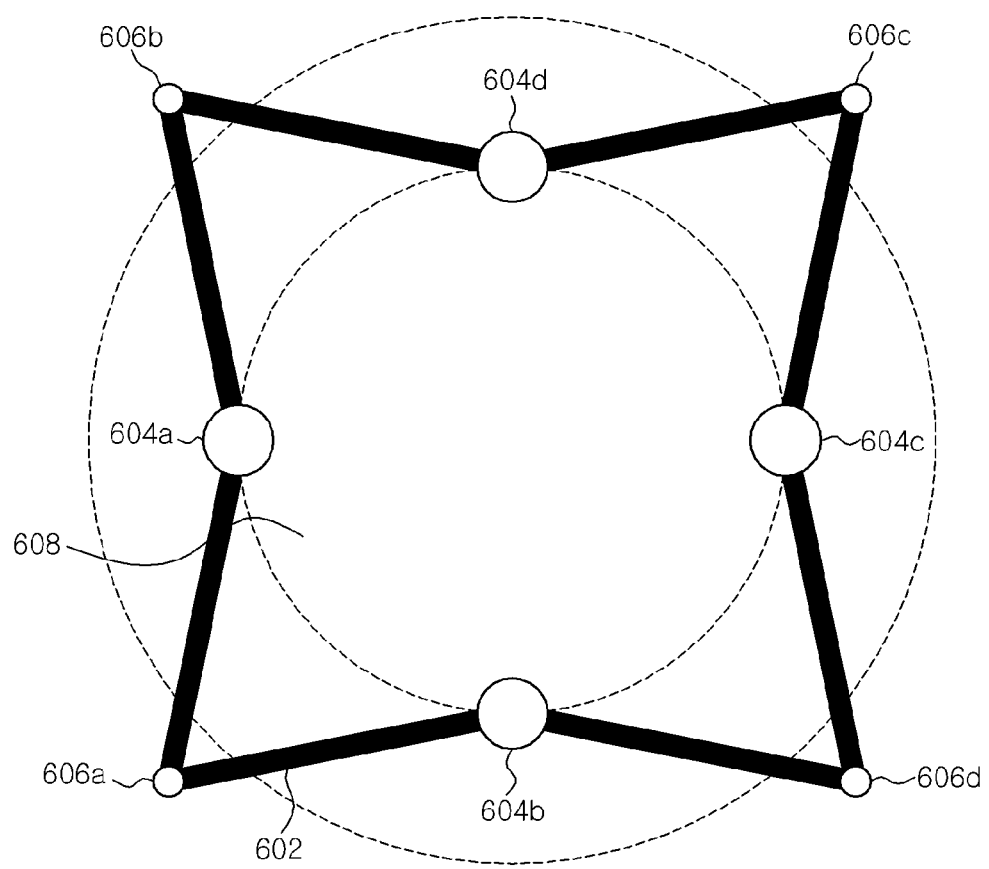
FIG. 6 shows a reduced structure of a sensor for a microwave image to which a folding scheme has been applied in accordance with yet another embodiment of the present invention.
Figure 7:
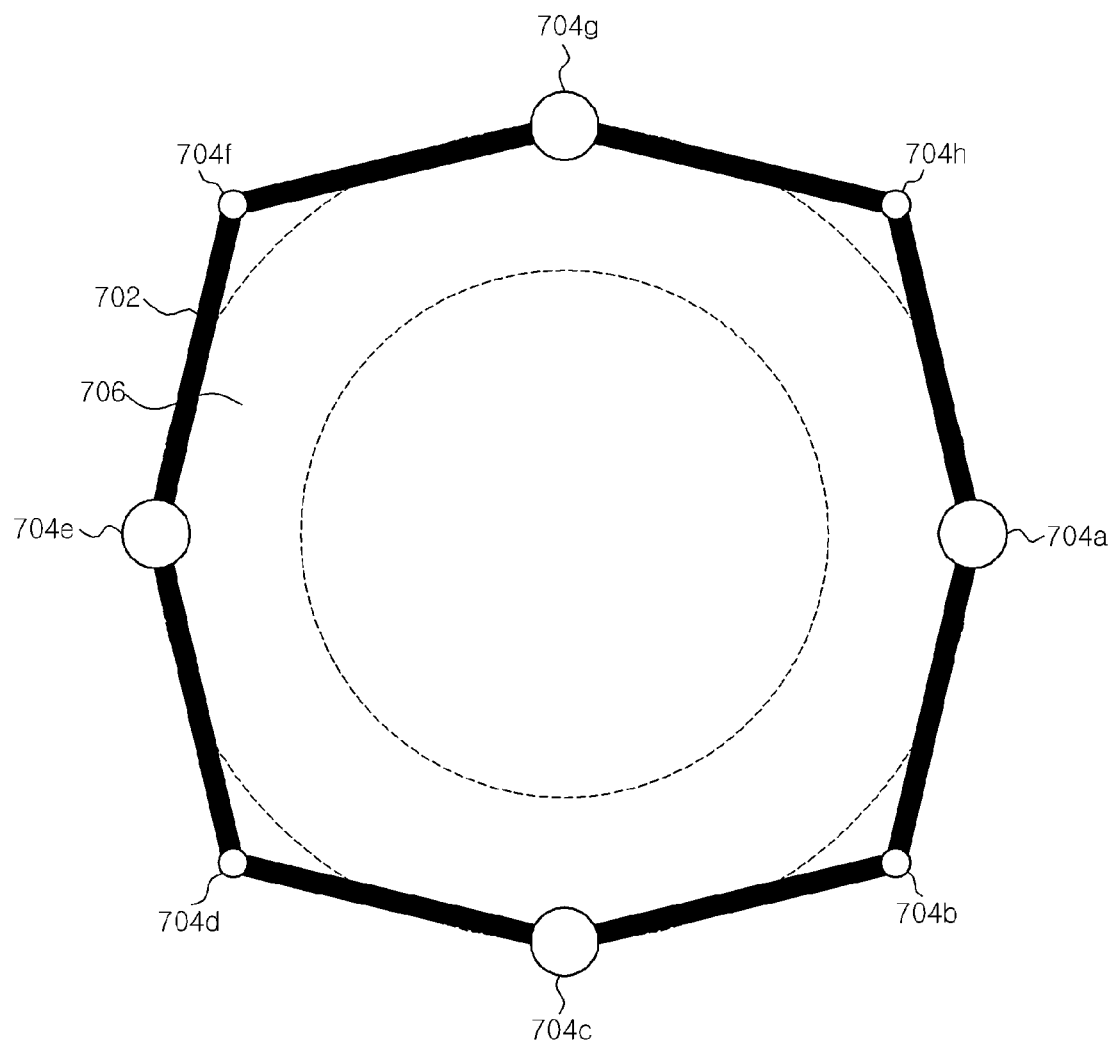
FIG. 7 shows an enlarged structure of a sensor for a microwave image to which a folding scheme has been applied in accordance with yet another embodiment of the present invention.

For example, as shown in FIGS. 5 to 7, a polygonal structure can be applied to the metal body that forms the sensor for a microwave image in accordance with the present embodiment. In an embodiment, a structure in which the receipt width (or size) of a tank can be changed (e.g., a partial folding or a slidable hinge structure) can be applied to the metal body using a folding scheme (or a partial folding scheme).

FIG. 5 shows the structure of a sensor for a microwave image in accordance with another embodiment of the present invention, FIG. 6 shows a reduced structure of a sensor for a microwave image to which a folding scheme has been applied in accordance with yet another embodiment of the present invention, and FIG. 7 shows an enlarged structure of a sensor for a microwave image to which a folding scheme has been applied in accordance with yet another embodiment of the present invention.

Referring to FIG. 5, in accordance with the present embodiment, a metal body 504 in which a plurality of apertures #1 to #N is formed (fixed and disposed) at constant intervals inside the metal body 504, that is, on the inside in which a tank 502 is formed, can be configured to have a polygonal structure in which an edge is formed between neighboring apertures. If the metal body 504 has such a polygonal structure, a sensor for a microwave image can be adaptively applied depending on a shape of human tissue for image sensing.

Referring to FIG. 6, each of apertures 604a to 604d and 606a to 606d formed at constant intervals in a metal body 602 is configured to be partially folded such that the apertures 604a to 604d and 606a to 606d are partially folded in such a manner that some apertures 604a to 604d are placed relatively inside and the remaining apertures 606a to 606d are placed relatively outside. In this case, the receipt width (or size) of a tank 608 for receiving an image object can be relatively reduced (i.e., variable reduction). The partial folding can be defined as partial folding on the basis of each aperture.

Referring to FIG. 7, apertures 704a to 704h formed at constant intervals in a metal body 702 can be configured to be partially folded so that all the apertures 704a to 704h are spread outward. Accordingly, when compared with the tank of FIG. 6, the receipt width of a tank 706 can be relatively enlarged (i.e., variable enlargement).

Embodiment 2

Figure 8:
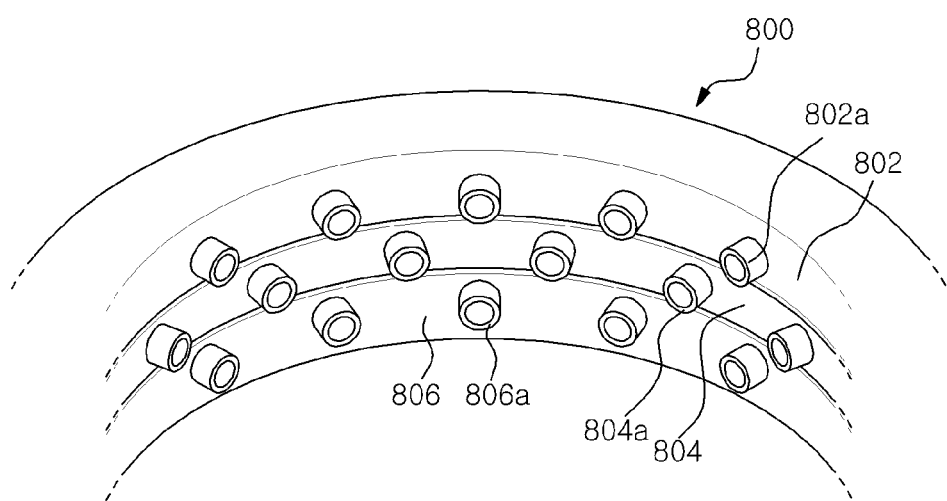
FIG. 8 shows the structure of a sensor for a microwave image in accordance with yet another embodiment of the present invention.

FIG. 8 shows the structure of a sensor for a microwave image in accordance with yet another embodiment of the present invention.

Referring to FIG. 8, a metal structure applied to the sensor for a microwave image in accordance with the present embodiment is configured to surround a tank (i.e., a tank filled with a matching medium in the same manner as or similarly to Embodiment 1) including a plurality of apertures formed at constant intervals inside the metal structure. In such a structure, a metal body in which when any one of the plurality of apertures radiates microwaves to an image object, the remaining apertures receive scattering microwaves from the image object has a plurality of layers (e.g., 2 layers, 3 layers, 4 layers, or 5 layers).

That is, for example, as shown in FIG. 8, a metal structure 800 of the present embodiment can be configured to have a structure in which a first metal body 802 having a plurality of apertures 802a formed therein at constant intervals, a second metal body 804 having a plurality of apertures 804a formed therein at constant intervals, and a third metal body 806 having a plurality of apertures 806a formed therein at constant intervals are sequentially stacked in a vertical direction.

Each of the first to third metal bodies 802, 804, and 806 that form the body structure 800 may be configured to rotationally move in a direction different from that of a neighboring metal body. In this case, image sensing can be adaptively changed if necessary or according to use.

In an embodiment, the body structure 800 of the present embodiment may be configured to have a ring-shaped structure or a polygonal structure as in Embodiment 1. The inside of each of the metal bodies 802, 804, and 806 may be configured to have an edge angle formed by a mountain and a valley between neighboring apertures, an approximately central part of the inside of each metal body that connects neighboring apertures may be configured to form a mountain, or the front of the inside of the metal body may be configured to have a wrinkle structure (or wrinkle shape). In an embodiment, the metal body may be configured to have a partial folding structure which can partially fold (slide) on the basis of each aperture.

While the invention has been shown and described with respect to the preferred embodiments, the present invention is not limited thereto. It will be understood by those skilled in the art that various changes and modifications may be made without departing from the scope of the invention as defined in the following claims.

Accordingly, the scope of the present invention should be interpreted based on the following appended claims, and all technical spirits within an equivalent range thereof should be construed as being included in the scope of the present invention.

What is claimed is:

1. A sensor for a microwave image, comprising:
   a tank filled with a matching medium;
   a metal body having a ring-shaped or polygonal structure, and being configured to surround an image object received in the tank through the metal body; and
   a plurality of apertures disposed at constant intervals inside the metal body and directed at a center of the ring-shaped or polygonal structure;
   wherein when any one of the plurality of apertures radiates microwaves to the image object, remaining apertures receive scattering microwaves from the image object.

2. The sensor of claim 1, wherein the matching medium has a dielectric constant identical with a dielectric constant of the image object.

3. The sensor of claim 1, wherein the matching medium is a loss matching medium of a liquid phase.

4. The sensor of claim 1, wherein the matching medium is a non-loss matching medium of gas or a dielectric solid.

5. The sensor of claim 1, wherein the metal body senses an image of the image object through a rotational movement and a vertical movement.

6. The sensor of claim 1, wherein the inside of the metal body is configured to have edge angles formed by mountains and valleys.

7. The sensor of claim 1, wherein the inside of the metal body has a wrinkle structure.

8. The sensor of claim 1, wherein if the metal body has the polygonal structure, a receipt width of the image object is changed by partial folding based on at least any one of the plurality of apertures.

9. The sensor of claim 1, wherein the image object is any one of human tissues for an image diagnosis.

10. A sensor for a microwave image, comprising:
   a tank filled with a matching medium; and
   a body structure formed of a plurality of metal bodies in plural layers, each metal body having a ring-shaped or polygonal structure, the metal bodies having a plurality of apertures disposed at constant intervals inside the metal body and directed at a center of the ring-shaped or polygonal structure, to surround an image object received in the tank through the metal body, and
   wherein when any one of the plurality of apertures radiates microwaves to the image object, remaining apertures receive scattering microwaves from the image object.

11. The sensor of claim 10, wherein each of the metal bodies forming the body structure is configured to rotationally move in a direction different from a direction of a neighboring metal body.

12. The sensor of claim 10, wherein the matching medium has a dielectric constant identical with a dielectric constant of the image object.

13. The sensor of claim 10, wherein the matching medium is a loss matching medium of a liquid phase.

14. The sensor of claim 10, wherein the matching medium is a non-loss matching medium of gas or a dielectric solid.

15. The sensor of claim 10, wherein the body structure senses an image of the image object through a rotational movement and a vertical movement.

16. The sensor of claim 10, wherein the inside of each of the metal bodies forming the body structure is configured to have edge angles formed by mountains and valleys.

17. The sensor of claim 10, wherein the inside of each of the metal bodies forming the body structure is configured to have a wrinkle structure.

18. The sensor of claim 10, wherein the image object is any one of human tissues for an image diagnosis.

* * * * *